(12) United States Patent
Wu et al.

(10) Patent No.: US 9,217,669 B2
(45) Date of Patent: Dec. 22, 2015

(54) ONE-DIMENSIONAL GLOBAL RAINBOW MEASUREMENT DEVICE AND MEASUREMENT METHOD

(71) Applicant: ZHEJIANG UNIVERSITY, Hangzhou, Zhejiang (CN)

(72) Inventors: Xuecheng Wu, Hangzhou (CN); Kefa Cen, Hangzhou (CN); Zhihua Wang, Hangzhou (CN); Xiang Gao, Hangzhou (CN); Linhong Chen, Hangzhou (CN); Kunzan Qiu, Hangzhou (CN); Yingchun Wu, Hangzhou (CN); Haoyu Jiang, Hangzhou (CN)

(73) Assignee: ZHEJIANG UNIVERSITY, Hangzhou, Zhejiang (CN)

( * ) Notice: Subject to any disclaimer, the term of this patent is extended or adjusted under 35 U.S.C. 154(b) by 0 days.

(21) Appl. No.: 14/356,723

(22) PCT Filed: May 10, 2013

(86) PCT No.: PCT/CN2013/075434
§ 371 (c)(1),
(2) Date: May 7, 2014

(87) PCT Pub. No.: WO2014/179976
PCT Pub. Date: Nov. 13, 2014

(65) Prior Publication Data
US 2015/0177065 A1    Jun. 25, 2015

(51) Int. Cl.
*G01J 3/46* (2006.01)
*G01J 3/14* (2006.01)
*G01N 15/02* (2006.01)
*G01J 3/28* (2006.01)
*G01N 15/00* (2006.01)

(52) U.S. Cl.
CPC .................. *G01J 3/14* (2013.01); *G01J 3/2823* (2013.01); *G01J 3/46* (2013.01); *G01N 15/0211* (2013.01); *G01N 2015/0046* (2013.01); *G01N 2015/0277* (2013.01)

(58) Field of Classification Search
CPC .................. G01J 3/46; G01J 3/50; G01J 3/51; G01J 3/524; G01J 3/02
USPC .................................................. 356/300–445
See application file for complete search history.

(56) References Cited

U.S. PATENT DOCUMENTS

2007/0091325 A1* 4/2007 Nikoonahad .................. 356/625
2008/0037031 A1* 2/2008 Cole et al. ..................... 356/601

* cited by examiner

*Primary Examiner* — Abdullahi Nur
(74) *Attorney, Agent, or Firm* — Kratz, Quintos & Hanson, LLP

(57) ABSTRACT

The present invention provides a one-dimensional global rainbow measurement device and a measurement method. The measurement device comprises three parts, i.e., a laser emission unit, a signal collection unit and a signal processing unit. The laser emission unit is modulated to be a light sheet by a laser beam emitted by a laser, and configured to irradiate droplets in a spray field to generate rainbow signals. The signal collection unit is configured to separately image, by an optical system unit, the rainbow signals at measurement points of different height onto different row pixels of a CCD signal collector. The signal processing unit is configured to convert the received rainbow signals and process by a computer the rainbow signals in a form of data to obtain the measured values. The present invention can analyze gas-liquid phase flow fields during the injection, realize the online measurement of fuel atomization, spray and other processes, and can measure the refractive index, size, temperature and other parameters of the spray droplets in a real-time and non-contact manner.

12 Claims, 3 Drawing Sheets

ONE-DIMENSIONAL GLOBAL RAINBOW MEASUREMENT DEVICE AND MEASUREMENT METHOD

TECHNICAL FIELD

The present invention relates to the field of gas-liquid two-phase flow measurement, particularly to global rainbow measurement device and method for measuring the size, refractive index, temperature and other parameters of spray droplets in a one-dimensional manner.

BACKGROUND OF THE INVENTION

Spray is a common gas-liquid two-phase flow phenomenon in the filed of energy environment at present, for example, atomization, evaporation and combustion of liquid fuel, gas-liquid mixture and absorption in a desulfurization and denitrification rainmaker, etc. In the art, there have been various techniques for measuring a spray field. Conventional contact measurement methods include: immersion, tracking, sedimentation, freezing, wax melting, instant sampling, etc. The methods as mentioned above may damage the original flow field, resulting in errors and great limitations in application, and are thus not applicable to the present measurement requirements. However, many laser measurement techniques have broken the above limitations and have advantages of no interference to the original flow field, high precision, real-time and quick measurement, large volume of information, availability of quantitative calculation and the like.

According to the measurement category of laser techniques, the common methods for measuring the size of spray droplets include Melvin granulometer, laser MIE scatter, laser-induced fluorescence, laser holography, laser photomicrography, Interferometric Laser Imaging Droplet Sizing (IL-IDS), and Phase Doppler Anemometry (PDPA or PDA); the common methods for measuring the refractive index of spray droplets include V-shape prism, glancing incidence (Abbe refractor), and interference fringe (Newton ring); the methods for measuring the temperature of spray droplets mainly include fluorescence and rainbow scattering, the latter can measure the size of droplets or size distribution simultaneously and is classified into two forms, i.e., standard rainbow and a global rainbow; in addition, the common methods for measuring the concentration of a spray field include pseudocolor, shadow and Computerized Tomography (CT); and the common methods for measuring the speed of a spray field include Laser Doppler Velocimetry or Laser Doppler Anemometry (LDV or LDA), Light Speckle Velocimetry (LSV), Phase Doppler Anemometry (PDPA or PDA) and Particle Image Velocimetry (PIV).

The principle of the Global Rainbow Technique (GRT) is that light is irradiated onto spherical particles, a part of the light is incident on the balls and then emitted from the balls after reflected primarily by the inner surfaces of the balls (known as First-order Rainbow) while another part of the light is reflected by the outer surfaces of the balls. The reflected light and the emergent light resulted from the primary internal reflection are interfered with each other to form a series of intensity oscillating ripples. As there are multiple kinds of obvious oscillation of different frequency in the rainbow signals, it is required to filter high-frequency oscillation structures to form smooth rainbow signals. By recording the prolonged time of exposure and the expanded clear aperture, the rainbow of thousands of droplets having a certain size distribution is recorded. As the scattered light of various particles is overlapped with each other, the high-frequency ripple signals attached to a single particle of first-order rainbow are eliminated, so that the rainbow signals may be smoothened, and then the average refractive index, size distribution, average temperature and other parameters of the spray droplets are thus inverted.

As the global rainbow technique has a unique advantage of measuring both the size and the reflective index to further invert the temperature and other parameters of the droplets, in the measurement of the spray flow field, the global rainbow technique and the related applications attract the attention of researchers all over the world. Van Beeck et al., from University of Brussels, have measured the liquid-liquid suspension, two-phase jet flow, and droplet evaporation and diffusion based on the rainbow technique. G. Grehan team, from France, has done a lot of research on the global rainbow technique in measuring the reflective index, reflective index gradient, temperature and size distribution of droplets, and has applied the global rainbow technique in complicated and harsh sites for measurement. S. Bakic et al., from Darmstadt University of Technology in Germany, have applied the global rainbow technique to the component measurement during the evaporation of bi-component droplets. J. Wilms et al., from Stuttgart University in Germany, have measured the change of component during the evaporation of a single bi-component droplet based on the rainbow technique. The S. Sankar team, from America, has done research on the heating and evaporation characteristics of fuel droplets based on the rainbow temperature measurement technique, and has used the rainbow technique together with the PDA in measuring the combustion particulates. H. Lohner et al., from Bremen University in Germany, have done research on the non-spherical degree of droplets when measuring the liquid-liquid suspension based on the rainbow technique. V. Bodoc et at., from France, have researched the evaporation of bi-component droplets under a turbulent environment within a passage based on the rainbow technique. Wu Xuecheng, Wu Yingchun, et al., from Zhejiang University, have done simulation and experimental researches on the measurement of size, concentration and temperature of spray droplets, the measurement of components of complex bi-spray, and the volume ratio of all components, based on the global rainbow technique.

So far, the global rainbow technique is restricted to single-point measurement. The global rainbow technique may provide a better test tool for researches on the non-steady-state complex spray flow fields If one-dimensional, two-dimensional and even three-dimensional global rainbow techniques are further developed, which will be of great significance in the further in-depth study of the spray mechanism.

SUMMARY OF THE INVENTION

An object of the present invention is to provide a global rainbow measurement device and a measurement method capable of performing one-dimensional measurement of size, reflective index and temperature of spray droplets, in order to overcome the defect that the existing global rainbow technique is restricted to single-point measurement. The device and method as provided by the present invention can analyze gas-liquid phase flow fields during the injection, realize the online measurement of fuel atomization, spray and other processes, and can measure the refractive index, size, temperature and other parameters of the spray droplets in a real-time and non-contact manner.

To solve the above technical problem, the present invention employs the following specific technical solutions.

A one-dimensional global rainbow measurement device is provided, comprising three parts, i.e., a laser emission unit, a signal collection unit and a signal processing unit:

a. the laser emission unit is modulated to be a light sheet by a laser beam emitted by a laser, and configured to irradiate droplets in a spray field to generate rainbow signals;

b. the signal collection unit is configured to separately image, by an optical system unit, the rainbow signals at measurement points of different height onto different row pixels of a CCD signal collector; and c. the signal processing unit is configured to convert the received rainbow signals and process the rainbow signals in a form of data to obtain the measured values by a computer.

In the present invention, the polarized light sheet provided by the laser emission unit irradiates onto a measurement area of the spray field to generate rainbow signals from the spray droplets. After passing through the optical system unit, the rainbow signals at measurement points of different height are separately imaged onto different row pixels of the CCD signal collector, so that rainbow signals of a one-dimensional line area are obtained at one time. By performing the conventional single-point GRT inversion algorithm to the collected one-dimensional rainbow signals, the size distribution and reflective index distribution of the spray droplets at each point on the one-dimensional line may be obtained; and, as temperature, components (compositions) and other physical parameters have a certain specific change along with the reflective index, the temperature distribution, component distribution and other key parameters of a spray field may be inverted according to the obtained reflective index distribution. The device and method as provided by the present invention overcomes the defect that GRT in the prior art is restricted to single-point measurement, realizes the one-dimensional measurement of a complex spray field by a global rainbow measurement system, and is characterized by simple structure and applicability for industrial online application, etc. Furthermore, the device and method as provided by the present invention can perform one-time measurement to rainbow signals of spray droplets of different height on a one-dimensional line to obtain the size and reflective index distribution thus to quickly obtain the size, temperature and other parameters of the spray droplets in real time. In addition, by continuously collecting data of one-dimensional spray droplets, the parameter distribution of a two-dimensional steady spray field may be also obtained.

Preferably, the laser emission unit consists of the following three parts:

a semiconductor laser, configured to generate an intensity adjustable laser beam;

a modulator element, configured to modulate the emergent laser beam into a polarized light sheet; and a bench system, configured to adjust the incident position and incident angle of the laser light sheet so that the direction of rainbow signals generated by the spray droplets coincides to the primary optical axis of the optical system unit.

Preferably, the semiconductor laser is a 40 mW-600 mW intensity adjustable laser fixed on a rotary stage of which the repeat positioning accuracy is less than 0.005 and the resolution is 0.00125°.

Preferably, the modulator element comprises a polarizer, a beam expander and a cylindrical lens, the semiconductor laser, the beam expander and the cylindrical lens being disposed on the bench system. The laser beam emitted from the semiconductor laser passes through the polarizer so that linearly polarized waves (TM waves) having magnetic vectors vertical to the incidence plane are allowed to pass therethrough, and is then expanded by the beam expander and modulated into a light sheet by the cylindrical lens, and finally irradiated onto the measurement area of the spray field.

Preferably, the signal collection unit comprises a field lens, a horizontal diaphragm, a vertical diaphragm, an imaging lens and a CCD signal collector, the horizontal diaphragm being provided on the rear side of the field lens, light reflected from the spray field passing through the field lens, the horizontal diaphragm, the vertical diaphragm and the imaging lens in turn and then entering the CCD signal collector. The field lens having the horizontal diaphragm, the vertical diaphragm and the imaging lens form a Fourier optical imaging system of the one-dimensional global rainbow measurement system. The rainbow signals of droplets of different height are collected by the field lens. The horizontal diaphragm is provided on the rear side of the field lens, and configured to allow only the rainbow signals passing through the horizontal center line of the lens to pass through the lens. As a result, the rainbow signals at measurement points of different height have different incident angles, and then may be separated based on the Fourier imaging principle to be imaged onto different row pixels of the CCD signal collector. The vertical diaphragm is disposed at a position where the measurement area is corresponding to the image plane of the field lens, and may be configured to control the size of the measurement area.

Preferably, the line width of the horizontal diaphragm on the front side of the field lens is 0.5 mm-5 mm; and the vertical diaphragm is a zero-aperture iris diaphragm having a maximum aperture width of 25 mm.

Preferably, both the field lens and the imaging lens are 80 mm-120 mm in diameter and 100 mm-250 mm in focal length.

Preferably, the CCD chip of the CCD signal collector is a linear CCD, of which, the range of pixels is 1M-16M, the maximum frequency is 30 Hz, the range of detecting rainbow angle is 10°-20°, and the angle of minimum resolution is 0.002°. According to different measurement objects and measurement conditions, the time of CCD exposure and the angle and intensity of the emergent light may be adjusted thus to achieve a better measurement effect.

Preferably, the COD signal collector is provided thereon with a height adjustor. The height adjustor is configured to adjust the height of a photosensitive surface of a receiving portion of a detector.

Preferably, a filter is provided in front of the CCD signal collector. The filter is configured to reduce the power of background light received by the CCD signal collector and thus to reduce the scattering of peripheral light and the noise resulted from background radiation. Under the premise of allowing lasers to pass through, the bandwidth of the filter should be as narrow as possible so that the detector is allowed to stay in a good working state.

A measurement method by using a one-dimensional global rainbow measurement device is provided, comprising the following steps of:

a. calibrating the rainbow signal height and scattering angle of a light path by using a laser;

b. opening a nozzle device, and adjusting a spray field to a steady state;

c. turning on the laser, a laser beam emitted by the laser being expanded by a beam expander and then passing through cylindrical lens to irradiate onto a measurement area of the spray field in a form of vertically polarized light sheet, rainbow signals scattered from the spray droplets of different height passing through a field lens having a horizontal diaphragm to allow only the rainbow signals passing through the horizontal center line of the lens to pass through the lens, the rainbow signals of droplets of different height thus being separated due to different incident angles;

d. adjusting the aperture width of a vertical diaphragm between the field lens and imaging lens, controlling the size of the field area and filtering environmental stray light until clear and stable rainbow signals are obtained; and e. by the imaging lens, refracting scattering pattern strips of different angles which have passed through the field lens onto a CCD chip, light of different emission angles being corresponding to different rows on a pixel plane of the CCD signal collector, pixels in each row recording at different scattering angles the light intensity of the spray droplets at points of different height.

Preferably, the method for calibrating a scattering angle comprises the following steps of:

providing a reflective mirror with a rotary stage in the measurement area of the spray field in the extension direction of the primary optical axis of the optical system unit; adjusting the rotary stage so that the light reflected by the reflective mirror coincides to the primary optical axis of the optical system unit, and recording the initial angle of the rotary stage; fine tuning the rotation angle of the rotary stage, and recording the rotation angle and the position of the reflected light on the CCD signal collector to obtain the scattering angle of a calibration point in combination with the angle between the laser beam emitted by the laser and the primary optical axis of the optical system unit and further to obtain the relationship between the pixels of the CCD signal collector and the scattering angle.

The present invention has the following advantages: the device and method as provided by the present invention overcomes the defect that GRT in the prior art is restricted to single-point measurement, realizes the one-dimensional measurement of a complex spray field by a global rainbow measurement system, and is characterized by simple structure and applicability for industrial online application, etc. Furthermore, the device and method as provided by the present invention can perform one-time measurement to rainbow signals of spray droplets of different height on a one-dimensional line to obtain the size and reflective index distribution thus to quickly obtain the size, temperature and other parameters of the spray droplets in real time. In addition, by continuously collecting data of one-dimensional spray droplets, the parameter distribution of a two-dimensional spray may can be also obtained. Moreover, the device and method as provided by the present invention are advantageous to the monitoring analysis of practical industrial applications, and provide data guidance for control strategies and design schemes of combustion and pollutants, thereby saving raw materials and reducing emission.

In addition, the dynamic change of a spray field under heating, cooling or other complex environmental conditions may be measured by using a spray device of rational design. By measuring a mixed complex spray field having multiple components, the volume fraction of each component within a measurement area may be inverted from the obtained mixed rainbow diagram.

In the figures: 1-Laser; 2-Polarizer; 3-Beam expander; 4-Cylindrical lens; 5-Field lens; 6-Horizontal diaphragm; 7-Vertical diaphragm; 8-Imaging lens; 9-Filter; 10-CCD signal collector; 11-Spray field; 12-Spray droplets; 13-Nozzle device; and, 14-Rainbow signals.

DETAILED DESCRIPTION OF THE INVENTION

The specific implantations of the technical solutions of the present invention will be further described as below with reference to accompanying drawings by embodiments.

Embodiment 1

Figure 1:
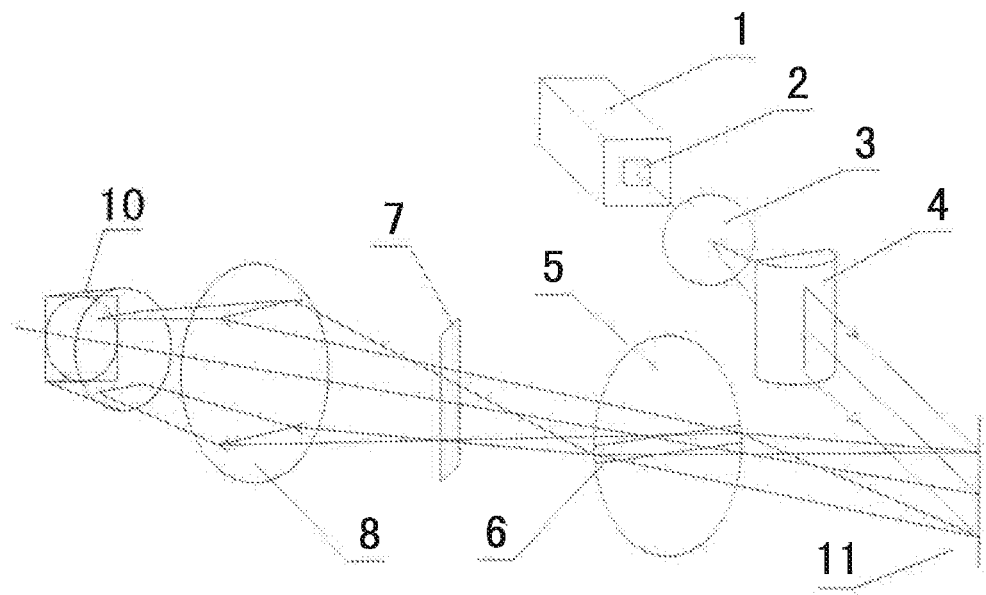
FIG. 1 is an overall structure diagram of Embodiment 1 of a one-dimensional global rainbow measurement device according to the present invention.
Figure 2:
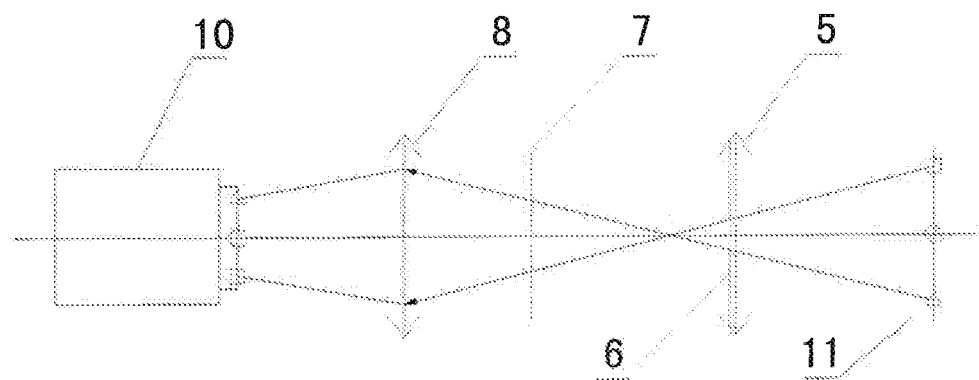
FIG. 2 is a structure diagram of a light path of an optical system unit of Embodiment 1 of the one-dimensional global rainbow measurement device according to the present invention.
Figure 5:
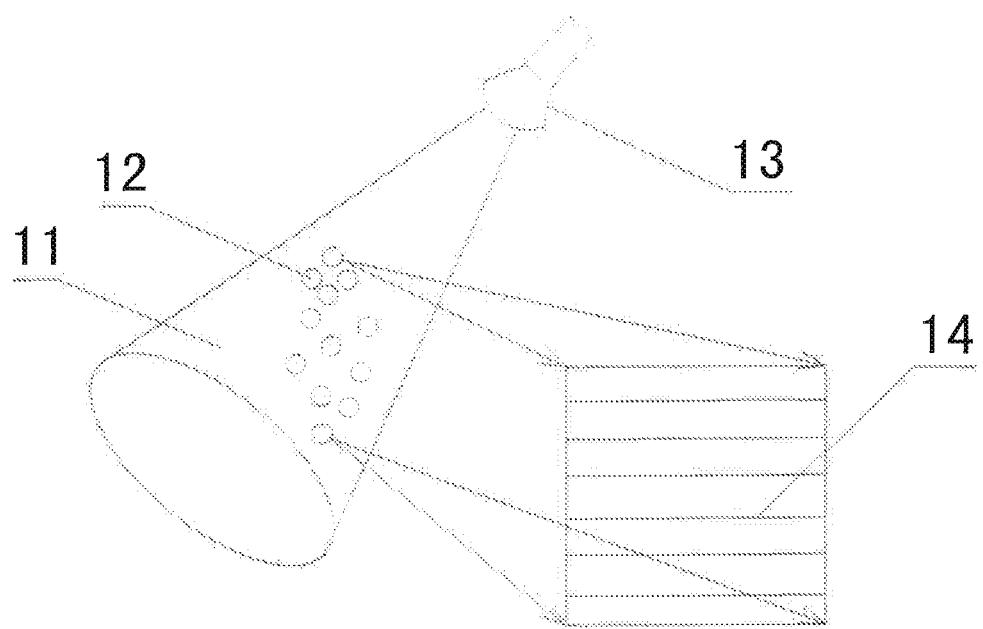
FIG. 5 is an amplified structure diagram of an interference image of a spray field and rainbow signals of spray droplets according to the present invention.

In Embodiment 1 as shown in FIG. 1 and FIG. 2, a one-dimensional global rainbow measurement device is provided, comprising three parts, i.e., a laser emission unit, a signal collection unit and a signal processing unit.

a. The laser emission unit is modulated to be a light sheet by a laser beam emitted by a laser, and configured to irradiate droplets in a spray field to generate rainbow signals. The laser emission unit consists of the following three parts:

a semiconductor laser 1, configured to generate an intensity adjustable laser beam, the semiconductor laser in this embodiment being a 40 mW-600 mW intensity adjustable laser fixed on a rotary stage of which the repeat positioning accuracy is less than 0.005 and the resolution is 0.00125°;

a modulator element, configured to modulate the emergent laser beam into a polarized light sheet, the modulator element comprising a polarizer 2, a beam expander 3 and a cylindrical lens 4; and a bench system, configured to adjust the incident position and incident angle of the laser light sheet so that the direction of rainbow signals 14 (referring to FIG. 5) generated by the spray droplets 12 coincides to the primary optical axis of the optical system unit, the semiconductor, the beam expander and the cylindrical lens being all disposed on the bench system.

b. The signal collection unit is configured to separately image, by an optical system unit, the rainbow signals at measurement points of different height onto different row pixels of a CCD signal collector 10, the signal collection unit comprising a field lens 5, a horizontal diaphragm 6, a vertical diaphragm 7, an imaging lens 8 and a CCD signal collector, the horizontal diaphragm being provided on the rear side of the field lens, light reflected from the spray field 11 passing through the field lens, the horizontal diaphragm, the vertical diaphragm and the imaging lens in turn and then entering the CCD signal collector. Both the field lens and the imaging lens are 80 mm-120 mm in diameter and 100 mm-250 mm in focal length. The CCD chip of the CCD signal collector is a linear CCD, of which, the range of pixels is 1M-16M, the maximum frequency is 30 Hz, the range of detecting rainbow angle is 10°-20°, and the angle of minimum resolution is 0.002°. The CCD signal collector is provided thereon with a height adjustor.

c. The signal processing unit is configured to convert the received rainbow signals and process the rainbow signals in a form of data to obtain the measured values by a computer.

A measurement method by using a one-dimensional global rainbow measurement device is provided, comprising the following steps of:

a. calibrating the rainbow signal height and scattering angle of a light path by using a laser, in which the method for calibrating a scattering angle comprises the following steps of:

providing a reflective mirror with a rotary stage in the measurement area of the spray field in the extension direction of the primary optical axis of the optical system unit; adjusting the rotary stage so that the light reflected by the reflective mirror coincides to the primary optical axis of the optical system unit, and recording the initial angle of the rotary stage; fine tuning the rotation angle of the rotary stage, recording the rotation angle and the position of the reflected light on the CCD signal collector to obtain the scattering angle of a calibration point in combination with the angle between the laser beam emitted by the laser and the primary optical axis of the optical system unit and further to obtain the relationship between the pixels of the CCD signal collector and the scattering angle; and then synchronously adjusting the height of the reflective mirror and the height of the laser, and measuring the variation of the height and repeating the above measurement process to obtain the correspondence between measurement points of different height on a one-dimensional line in the spray field and the upper and lower pixel rows of the CCD signal collector;

b. opening a nozzle device 13, and adjusting a spray field to a steady state;

c. turning on the laser, a laser beam emitted by the laser being expanded by a beam expander and then passing through cylindrical lens to irradiate onto a measurement area of the spray field in a form of vertically polarized light sheet, rainbow signals scattered from the spray droplets of different height passing through a field lens having a horizontal diaphragm to allow only the rainbow signals passing through the horizontal center line of the lens to pass through the lens, the rainbow signals of droplets of different height thus being separated due to different incident angles;

d. adjusting the aperture width of a vertical diaphragm between the field lens and imaging lens, controlling the size of the field area and filtering environmental stray light until clear and stable rainbow signals are obtained; and e. by the imaging lens, refracting scattering pattern strips of different angles which have passed through the field lens onto a CCD chip, light of different emission angles being corresponding to different rows on a pixel plane of the CCD signal collector, pixels in each row recording at different scattering angles the light intensity of the spray droplets at points of different height.

d. A receiving and processing unit is configured to convert the received rainbow signals and process by a computer the rainbow signals in a form of data to obtain the measured values.

After the size distribution of the spray droplet at each point on the one-dimensional measurement line is obtained, the obtained size distribution is substituted into a system of intensity linear equations so that the reflective index distribution of spray droplets within the one-dimensional measurement area may be obtained; and, as temperature, components (compositions) and other physical parameters have a certain specific change along with the reflective index, the temperature distribution, component distribution and other key parameters of the spray field may be inverted according to the obtained reflective index distribution. The device and method as provided by the present invention overcomes the defect that GRT in the prior art is restricted to single-point measurement, realizes the one-dimensional measurement of a complex spray field by a global rainbow measurement system, and is characterized by simple structure and applicability for industrial online application, etc. Furthermore, the device and method as provided by the present invention can perform one-time measurement to rainbow signals of spray droplets of different height on a one-dimensional line to obtain the size and reflective index distribution thus to quickly obtain the size, temperature and other parameters of the spray droplets in real time. In addition, by continuously collecting data of spray droplets on the one-dimensional measurement line, the parameter distribution of a two-dimensional steady spray field may be also obtained.

In addition, the dynamic change of a spray field under heating, cooling or other complex environmental conditions may be measured by using a spray device of rational design. By measuring a mixed complex spray field having multiple components, the inverted fraction of each component within a measurement area may be inverted from the obtained mixed rainbow diagram.

Embodiment 2

Figure 3:
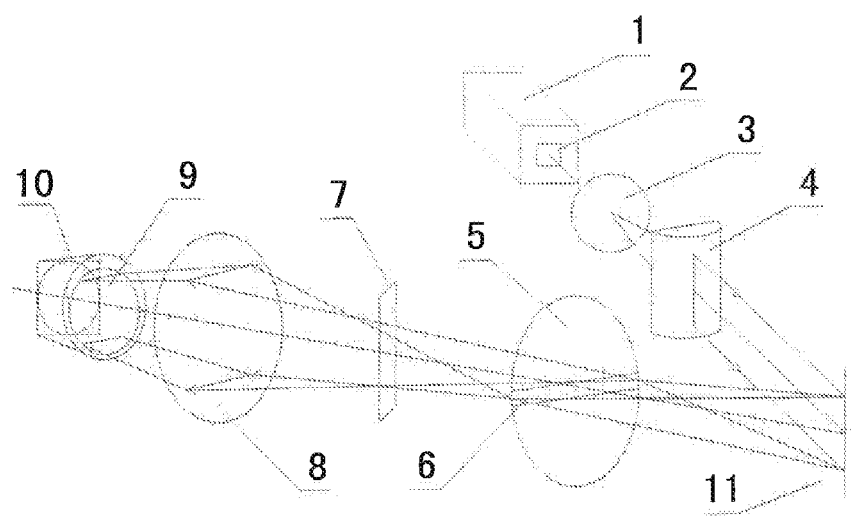
FIG. 3 is an overall structure diagram of Embodiment 2 of a one-dimensional global rainbow measurement device according to the present invention.
Figure 4:
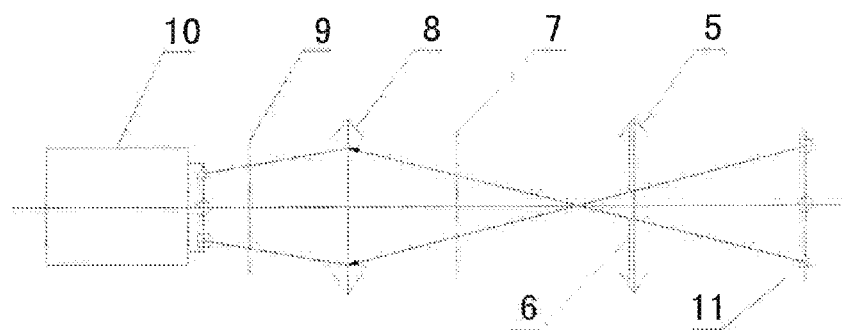
FIG. 4 is a structure diagram of a light path of an optical system unit of Embodiment 2 of the one-dimensional global rainbow measurement device according to the present invention.

A filter 9 (referring to FIG. 3 and FIG. 4) is provided in front of the CCD signal collector in Embodiment 2, the semiconductor laser is a 50 mW intensity adjustable laser, and the remaining is the same as that in Embodiment 1.

In this embodiment, the power of the semiconductor laser may be within 40 mW-600 mW. The line width of the horizontal diaphragm on the front side of the field lens may be within 0.5 mm-5 mm. The diameter of both the field lens and the imaging lens may be within 80 mm-120 mm, and the focal length of the both two may be within 100 mm-250 mm, Apart from the embodiments mentioned above, as long as not departing from the scope disclosed by the claims and specification of the present invention, the technical characteristics or technical data of the present invention may be reselected and combined to form new embodiments. However, these embodiments may be realized by those skilled in the art without any creative work, so these embodiments that have not been described in details here shall be regarded as specific embodiments of the present invention and fall into the protection scope of the present invention.

The invention claimed is:

1. A one-dimensional global rainbow measurement device, comprising three parts, i.e., a laser emission unit, a signal collection unit and a signal processing unit:
   a. the laser emission unit is modulated to be a light sheet by a laser beam emitted by a laser, and configured to irradiate droplets in a spray field to generate rainbow signals;
   b. the signal collection unit is configured to separately image, by an optical system unit, the rainbow signals at measurement points of different height onto different row pixels of a CCD signal collector; and
   c. the signal processing unit is configured to convert the received rainbow signals and process the rainbow signals in a form of data to obtain the measured values by a computer.

2. The one-dimensional global rainbow measurement device according to claim 1, characterized in that the laser emission unit consists of the following three parts:
   a semiconductor laser, configured to generate an intensity adjustable laser beam;

a modulator element, configured to modulate the emergent laser beam into a polarized light sheet; and a bench system, configured to adjust the incident position and incident angle of the laser light sheet so that the direction of rainbow signals generated by the spray droplets coincides to the primary optical axis of the optical system unit.

3. The one-dimensional global rainbow measurement device according to claim 2, characterized in that the semiconductor laser is a 40 mW-600 mW intensity adjustable laser fixed on a rotary stage of which the repeat positioning accuracy is less than 0.005 and the resolution is 0.00125°.

4. The one-dimensional global rainbow measurement device according to claim 2, characterized in that the modulator element comprises a polarizer, a beam expander and cylindrical lens, the semiconductor laser, the beam expander and the cylindrical lens being all disposed on the bench system.

5. The one-dimensional global rainbow measurement device according to claim 1, characterized in that the signal collection unit comprises a field lens, a horizontal diaphragm, a vertical diaphragm, an imaging lens and a CCD signal collector, the horizontal diaphragm being provided on the rear side of the field lens, light reflected from the spray field passing through the field lens, the horizontal diaphragm, the vertical diaphragm and the imaging lens in turn and then entering the COD signal collector.

6. The one-dimensional global rainbow measurement device according to claim 5, characterized in that the line width of the horizontal diaphragm on the front side of the field lens is 0.5 mm-5 mm; and the vertical diaphragm is a zero-aperture iris diaphragm having a maximum aperture width of 25 mm.

7. The one-dimensional global rainbow measurement device according to claim 5, characterized in that both the field lens and the imaging lens are 80 mm-120 mm in diameter and 100 mm-250 mm in focal length.

8. The one-dimensional global rainbow measurement device according to claim 1, characterized in that the CCD chip of the CCD signal collector is a linear COD, of which, the range of pixels is 1M-16M, the maximum frequency is 30 Hz, the range of detecting rainbow angle is 10°-20°, and the angle of minimum resolution is 0.002°.

9. The one-dimensional global rainbow measurement device according to claim 1, characterized in that the CCD signal collector is provided thereon with a height adjustor.

10. The one-dimensional global rainbow measurement device according to claim 1, characterized in that a filter is provided in front of the CCD signal collector.

11. A measurement method by using the one-dimensional global rainbow measurement device according to claim 1, comprising the following steps of:

a. calibrating the rainbow signal height and scattering angle of a light path by using a laser;

b. opening a nozzle device, and adjusting a spray field to a steady state;

c. turning on the laser, a laser beam emitted by the laser being expanded by a beam expander and then passing through cylindrical lens to irradiate onto a measurement area of the spray field in a form of vertically polarized light sheet, rainbow signals scattered from the spray droplets of different height passing through a field lens having a horizontal diaphragm to allow only the rainbow signals passing through the horizontal center line of the lens to pass through the lens, the rainbow signals of droplets of different height thus being separated due to different incident angles;

d. adjusting the aperture width of a vertical diaphragm between the field lens and imaging lens, controlling the size of the field area and filtering environmental stray light until clear and stable rainbow signals are obtained; and e. by the imaging lens, refracting scattering pattern strips of different angles which have passed through the field lens onto a CCD chip, light of different emission angles being corresponding to different rows on a pixel plane of the CCD signal collector, pixels in each row recording at different scattering angles the light intensity of the spray droplets at points of different height.

12. The measurement device of a one-dimensional global rainbow measurement device according to claim 11, characterized in that the method for calibrating a scattering angle comprises the following steps of:

providing a reflective mirror with a rotary stage in the measurement area of the spray field in the extension direction of the primary optical axis of the optical system unit; adjusting the rotary stage so that the light reflected by the reflective mirror coincides to the primary optical axis of the optical system unit, and recording the initial angle of the rotary stage; fine tuning the rotation angle of the rotary stage, recording the rotation angle and the position of the reflected light on the COD signal collector to obtain the scattering angle of a calibration point in combination with the angle between the laser beam emitted by the laser and the primary optical axis of the optical system unit and further to obtain the relationship between the pixels of the CCD signal collector and the scattering angle; and then synchronously adjusting the height of the reflective mirror and the height of the laser, and measuring the variation of the height and repeating the above measurement process to obtain the correspondence between measurement points of different height on a one-dimensional line in the spray field and the upper and lower pixel rows of the CCD signal collector.

\* \* \* \* \*